United States Patent
Arendash et al.

(10) Patent No.: US 11,752,356 B2
(45) Date of Patent: Sep. 12, 2023

(54) SYSTEMS FOR CONTROLLING POWER TO DIFFERENTLY LOADED ANTENNA ARRAYS

(71) Applicant: NeuroEM Therapeutics, Inc., Phoenix, AZ (US)

(72) Inventors: Gary W. Arendash, Phoenix, AZ (US); Rob Baranowski, Valley Center, CA (US)

(73) Assignee: NeuroEM Therapeutics, Inc., Tampa Bay, FL (US)

( * ) Notice: Subject to any disclaimer, the term of this patent is extended or adjusted under 35 U.S.C. 154(b) by 1196 days.

(21) Appl. No.: 16/273,519

(22) Filed: Feb. 12, 2019

(65) Prior Publication Data
US 2019/0168013 A1 Jun. 6, 2019

Related U.S. Application Data (63) Continuation-in-part of application No. 14/205,333, filed on Mar. 11, 2014, now Pat. No. 10,765,879.
(Continued)

(51) Int. Cl.
*A61N 1/40* (2006.01)
*H03G 3/30* (2006.01)
(Continued)

(52) U.S. Cl.
CPC .......... *A61N 1/40* (2013.01); *A61N 1/0476* (2013.01); *A61N 5/04* (2013.01); *H03G 3/30* (2013.01);
(Continued)

(58) Field of Classification Search
CPC .... A61N 1/0476; A61N 1/40; A61N 1/36025; A61N 2/004; A61N 2/02; A61N 2/006;
(Continued)

(56) References Cited

U.S. PATENT DOCUMENTS 5,441,532 A    8/1995  Fenn
6,248,126 B1   6/2001  Lesser
(Continued)

FOREIGN PATENT DOCUMENTS

EP    1907052       1/2010
EP    1606010 B1    2/2012
(Continued)

OTHER PUBLICATIONS

Nguyen, et al; "The Effect of a High Frequency Electromagnetic Field in the Microwave Range on Red Blood Cells"; Sep. 7, 2017.
(Continued)

*Primary Examiner* — Nguyen T Vo
(74) *Attorney, Agent, or Firm* — Nathan G. Guymon; Bamert Regan PLLC (57) ABSTRACT

In one example in accordance with the present disclosure, an antenna system is described. The antenna system includes an array of antennas. Each antenna emits electromagnetic waves and is presented with a load that is different from other antennas in the array. The antenna system also includes a control system. The control system includes a single transmitter to sequentially drive antenna sets, a switching device to select, for each activation period in an activation sequence, an antenna set to be driven, and a controller. The controller determines an actual power output of each antenna and generates an adjusted control signal for the single transmitter such that the output of each antenna is controlled to match a target power for that antenna, regardless of a load for the antenna.

20 Claims, 8 Drawing Sheets

Related U.S. Application Data (60) Provisional application No. 61/776,097, filed on Mar. 11, 2013.

(51) Int. Cl.
  *A61N 5/04* (2006.01)
  *A61N 1/04* (2006.01)
  *H01Q 1/27* (2006.01)

(52) U.S. Cl.
  CPC ......... *H03G 3/3036* (2013.01); *H03G 3/3042* (2013.01); *H01Q 1/273* (2013.01); *H03G 2201/103* (2013.01); *H03G 2201/106* (2013.01); *H03G 2201/307* (2013.01)

(58) Field of Classification Search
  CPC .. A61N 2005/0647; A61N 5/022; A61N 5/04; A61N 5/0624; A61B 5/4082; A61B 5/4088; A61B 5/4836; A61B 5/4848; A61B 5/6803; A61B 5/6844; H01Q 1/273; H03F 2200/451; H03F 3/19; H03G 2201/103; H03G 2201/106; H03G 2201/307; H03G 3/30; H03G 3/3036; H03G 3/3042
  See application file for complete search history.

(56) References Cited

U.S. PATENT DOCUMENTS

| | | |
|---|---|---|
| 6,334,069 B1 | 12/2001 | George |
| 6,410,137 B1 | 6/2002 | Bunyan |
| 6,463,336 B1 | 10/2002 | Mawhinney |
| 6,876,337 B2 | 4/2005 | Larry |
| 7,672,648 B1* | 3/2010 | Groe ............... H03G 3/3042 455/127.2 |
| 8,684,901 B1 | 4/2014 | Zabara |
| 8,868,177 B2 | 10/2014 | Simon et al. |
| 9,672,393 B1* | 6/2017 | Zhu ................ A61N 1/3787 |
| 10,792,483 B2 | 10/2020 | Andocs |
| 10,850,096 B2 | 12/2020 | Teng |
| 11,058,886 B1 | 7/2021 | Matloubian |
| 11,229,788 B1* | 1/2022 | John ................ A61N 2/006 |
| 2004/0122281 A1 | 6/2004 | Fischell |
| 2004/0127895 A1 | 7/2004 | Flock |
| 2004/0176805 A1 | 9/2004 | Whelan |
| 2004/0181115 A1 | 9/2004 | Sandyk et al. |
| 2004/0199070 A1 | 10/2004 | Krockel |
| 2005/0228209 A1 | 10/2005 | Schneider |
| 2006/0183995 A1 | 8/2006 | Bond |
| 2007/0244530 A1 | 10/2007 | Ren |
| 2008/0269851 A1 | 10/2008 | Deem |
| 2009/0131739 A1 | 5/2009 | Shalev |
| 2009/0156884 A1 | 6/2009 | Schneider |
| 2009/0276019 A1 | 11/2009 | Perez |
| 2010/0042168 A1 | 2/2010 | Pasche et al. |
| 2010/0114086 A1 | 5/2010 | Deem et al. |
| 2010/0210894 A1 | 8/2010 | Pasual-Leone |
| 2011/0230701 A1 | 9/2011 | Simon et al. |
| 2012/0065456 A1 | 3/2012 | Arendash et al. |
| 2012/0089201 A1 | 4/2012 | Pilla |
| 2012/0172954 A1* | 7/2012 | Zastrow ............ A61N 5/025 607/101 |
| 2012/0289869 A1 | 11/2012 | Tyler |
| 2013/0237742 A1* | 9/2013 | Capstick ........... A61B 18/1815 600/10 |
| 2014/0187851 A1 | 7/2014 | Cetroni |
| 2014/0228620 A1 | 8/2014 | Vasishta |
| 2014/0257017 A1* | 9/2014 | Arendash ............ A61N 1/40 600/13 |
| 2014/0303425 A1 | 10/2014 | Pilla |
| 2014/0330353 A1 | 11/2014 | Knight |
| 2015/0209566 A1 | 7/2015 | Peyman |
| 2015/0342661 A1 | 12/2015 | Ron Edoute |
| 2016/0022976 A1 | 1/2016 | Peyman |
| 2017/0014637 A1* | 1/2017 | Basser ............... A61N 1/40 |
| 2017/0065326 A1 | 3/2017 | Rosen |
| 2017/0209579 A1 | 7/2017 | Curley |
| 2018/0256911 A1* | 9/2018 | Funane ............... A61N 2/02 |
| 2019/0030354 A1* | 1/2019 | Turner ............... A61N 1/406 |
| 2019/0290355 A1 | 9/2019 | Amos |
| 2020/0038509 A1 | 2/2020 | Corr |
| 2020/0078600 A1 | 3/2020 | Dinh |
| 2020/0164195 A1 | 5/2020 | Lowsky |
| 2020/0297286 A1 | 9/2020 | Costa |
| 2020/0346028 A1 | 11/2020 | Arendash et al. |
| 2021/0153925 A1 | 5/2021 | Kim |
| 2021/0177491 A1 | 6/2021 | Onik |
| 2021/0220480 A1 | 7/2021 | Peyman |
| 2021/0338265 A1 | 11/2021 | Cohn |

FOREIGN PATENT DOCUMENTS

| | | |
|---|---|---|
| EP | 2414038 | 2/2012 |
| WO | WO-2007044386 | 4/2007 |
| WO | 2008008545 A3 | 9/2008 |
| WO | WO-2008141296 | 11/2008 |
| WO | 2017157874 A1 | 9/2017 |
| WO | 2020102312 A1 | 5/2020 |
| WO | 2020141527 A1 | 7/2020 |
| WO | 2020180653 A1 | 9/2020 |

OTHER PUBLICATIONS

Karsten, et al; "Red Blood Cells are Dynamic Reservoirs of Cytokines"; Feb. 15, 2018.

Gary W. Arendash, "Transcranial Electromagnetic Treatment Against Alzheimber's Disease: Why it has the Potential to Trump Alzheimer's Disease Drug Development," Journal of Alzheimer's Disease, 32 (Jun. 2012) pp. 243-266.

Rasouli; "Attenuation of interleukin-1 beta by pulsed electromagnetic fields after traumatic brain injury"; Neuroscience Letters 519 (2012) 4-8.

Merighi; "Signaling pathways involved in anti-inflammatory effects of Pulsed Electromagnetic Field in microglial cells"; Cytokine 125 (2020) 154777.

Peng Lihong et al., The Effect of Pulsed Electromagnetic Fields on Angiogenesis. Bioelectromagnetics, 42: 250-258, 2021, p. 251, col. 1, paragraph 3, col. 2, paragraphs 2-3, p. 254, col. 2, paragraph 2, p. 257, col. 2, paragraph 2.

Das Neves Sofia Pereira et al., CNS-Draining Meningeal Lymphatic Vasculature: Roles, Conundrums and Future Challenges, Frontiers Pharmacology, Apr. 28, 2021, vol. 12, p. 3, col. 1, last paragraph, p. 8, col. 2, last paragraph, p. 9, col. 1, paragraph 1.

Gerstner Elizabeth R. et al., AntiEndothelial Growth Factor Therapy for Malignant Glioma, Curr Neurol Neurosci Rep. May 2009, 9(3):254-262, p. 2, paragraphs 2-3.

* cited by examiner

SYSTEMS FOR CONTROLLING POWER TO DIFFERENTLY LOADED ANTENNA ARRAYS

RELATED APPLICATIONS

The present application claims benefit and is a continuation in part of U.S. application Ser. No. 14/205,333 filed Mar. 11, 2014, which claims the benefit of U.S. Provisional Application No. 61/776,097, filed Mar. 11, 2013. These applications are incorporated herein by reference in their entireties.

BACKGROUND

Someone in the world develops Alzheimer Disease (AD) every 3 seconds. AD, the most common form of dementia, is a debilitating neuro-degenerative disease in which one experiences confusion, memory impairment, language difficulty, and loss of bodily functions—often becoming fully dependent on others within 4 to 5 years of diagnoses. AD is responsible for 1 in 3 deaths of seniors and kills more people than breast and prostate cancer combined. Today, it is estimated that over 50 million people worldwide are living with AD—the prevalence is rising at an alarming rate and expected to double in the next 30 years.

Pharmaceutical companies have traditionally led the AD research effort. However, after tens of billions of dollars in research, AD remains neither preventable, curable, or even able to be slowed. An effective treatment or cure for AD is estimated to be worth more than $20b per year. Sadly, there are no products on the market that have been proven to cure the disease or even slow disease progression.

Other neuro-degenerative disease and neurological conditions similarly plague society with current treatments and/or cures proving ineffective.

BRIEF DESCRIPTION OF THE DRAWINGS

The accompanying drawings illustrate various examples of the principles described herein and are part of the specification. The illustrated examples are given merely for illustration, and do not limit the scope of the claims.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

As described above, AD is a neuro-degenerative disease which affects millions of lives and for which no pharmaceutical cure or treatment has been found. Where pharmaceutical solutions have failed, the innovative medical device as described herein, which uses Transcranial Electromagnetic Treatment (TEMT), provides a solution. The device shows unique potential to slow and/or potentially even reverse the effects of AD. The present device includes a skull cap affixed with multiple radio wave transmitting antennae connected to a control box worn on the arm. In some examples, the antennae may transmit radio frequency waves. However, in other examples, the electromagnetic waves may be applied at other frequencies. In these other examples, the system may include other components, such as coils or contact patches instead of antennas. The control system may include different components as well and may be placed at different locations on a patient's body. Treatment may be administered in-home by the patient's caregiver rather than through an out-patient facility. The device of the present specification, is the only technology under clinical development that targets both presumed causes of AD—the build-up of small β-amyloid (Aβ) oligomers and tau oligomers within nerve cells. A wide spectrum of pre-clinical studies show that the TEMT device has beneficial cognitive impact linked to disaggregation of toxic protein oligomers (especially Aβ) and brain mitochondrial enhancement in Alzheimer's animal models.

While specific reference is made to AD, the present system is also for the treatment of other neuro-degenerative diseases or neurological conditions such as Mild Cognitive Impairment (MCI), Mixed AD/Vascular Dementia, Cerebral Amyloid Angiopathy, Hemorrhagic Stroke, Multi-Infarct Dementia, Parkinson's Disease, Lewy Body Dementia, Down's Syndrome, Traumatic Brain Injury, Fronto-Temporal Lobe Dementia, Cerebral Traumatic Encephalopathy, Huntington's Disease, or Prion Diseases (Transmissive Spongiform Encephalopathy, Kuru, and Creutzfedt-Jakob Disease), Amyotrophic Lateral Sclerosis (ALS), mental retardation, stroke, autism, bipolar disorder, schizophrenia, anxiety disorders, mitochondrial encephalomyopathies, epilepsy, migraine headache, major depression, Dystonia, and Hemiballismus, Age-Associated Memory Impairment (AAMI), normal/unimpaired cognitive function, or subnormal cognitive function.

In order to deliver full brain TEMT, the device provides sequential, activation of multiple antennas positioned within the head unit such that only one antenna is active at any given time. Treatment may be administered if an antenna is active continuously. However, in some examples, pulsed energy may be more effective. Based on this more effective treatment and to maximize treatment for multiple areas of the brain, the present array system and electromagnet treatment device pulses energy into multiple antennas distributed around the head of a patient. Since a pulsed treatment includes periods of actively transmitting and being idle, the antenna system utilizes the idle time for one antenna to activate another antenna. As a specific example, for an antenna system with N antennas, if each antenna's active time is 1/N, the idle time outside this active time can be used to activate other antennas, and the areas of the brain that can be treated in the same treatment session is multiplied by N.

Operating the antenna system in this fashion maximizes brain coverage, however, there may be a need for a more focused deeper treatment in certain areas of the brain. This deeper penetration can be accomplished by simply simultaneously activating two or more antennas, which antennas are transmitting the same waveform. When multiple antennas are actively transmitting the same waveform, propagation waves are summed in the radiation field, producing peaks in specific areas in the field, thus allowing treatment energy to be focused in specific areas of the brain. If the phase of the signals to each of the active antennas is varied, the location of the peaks can be moved, steered, or focused to a particular location. This is referred to as beam forming. The combination of multiple antennas and the ability to beam form allows for complete coverage of all regions of the brain.

For practical use of a treatment device as described, the control system that generates the treatment waveforms used in the treatment should be as small as possible, allowing a patient to wear the device and be able to move around while wearing the device. A lower cost of the treatment device would open up the treatment options to a greater number of patients.

To accomplish the goals of smaller and lower cost, electronic circuit integration and reuse within the control unit is desirable. This plays in to every aspect of the product design, but presents challenges along the way, as current circuit designs may not exist that address the unique problems that arise from implementing a device with the requirements of the TEMT unit.

A small and low cost TEMT unit drives the need for the control unit to use a single transmitter and to have that transmitter's output distributed to each antenna at the appropriate time or with the appropriate power level and phase combination. This architecture is preferred over one that employs a dedicated transmitter for each antenna when the design goals of lower size and cost are taken into account.

However, driving different antennas from a single transmitter presents its own challenges. The largest challenge comes with power control of the transmitter. Transmission systems are designed to radiate a predetermined power level out of the antenna regardless of the loading that the antenna is subject to. As the load on the antenna changes, the load on the transmitter also changes, and the transmitter may have to work harder under some loading conditions to maintain the same output power level. In an example single-antenna scenario, a control loop monitors the transmitter's output power and adjusts the power level control on the transmitter, keeping the output power constant. This control loop may have a damped response, keeping the output power level from oscillating. In general, the load on the antenna changes relatively slowly as elements spatially vary in proximity to the antenna. Therefore, it is advantageous to have power control change slowly to maintain stability of the output power level.

When many antennas are driven by the same transmitter, each antenna may have a different load presented to it, which means that the transmitter's power output control should vary for each antenna as it drives it. In other antenna arrays, this is not an issue as the antennas in the array are generally mounted together and any material that is in proximity of one antenna is in proximity with the whole array, so the loading of the antennas within the array is very similar.

The TEMT device of the present system presents a unique challenge, as the antennas in the head unit will each have very different loading based upon how each one sits relative to the patient's head, scalp, and hair. As a specific example, a patient with full-bodied hair can be wearing the head cap of the TEMT device while sitting in a recliner, with the back of their head pressing against the recliner. In this scenario, the antennas in the back of the head will be very close to the materials in the recliner, which changes the load on those antennas. At the same time, the pressure of pressing against the recliner will compress the patient's hair and move those antennas closer to the scalp. Accordingly, the antennas at the back of the head will have scalp on one side and recliner on the other side in very close proximity. By comparison, the antennas on the front of the head will be held off somewhat from the scalp by the patient's hair, and will see free space loading on the outside of the antenna because there is nothing there. Thus, in this example the antenna loading between the front and back antennas will be dramatically different, and the transmitter should work at different levels to produce the same output power between the antennas, regardless of the difference in load. The loading in a TEMT device may vary much more significantly than what is seen in other antenna array systems. Current implementations do not account for significantly different loading between antennas within the array, as occur in the TEMT device.

In a sequential activation of antennas, the time to adjust the output power level of the transmitter comes during the short period when the antennas are being switched. Then, once the switch is completed, the power control again should have a damped response to keep the output power level stable. This combination is difficult to achieve in an inexpensive way that does not add significant complexity to the implementation circuitry.

Therefore, the present specification describes a small and low-cost system that can adjust the power output and phase from a single transmitter for use in an antenna array where the loading on each of the antennas can vary significantly.

The present specification describes systems, methods, and devices that address the above-described problems and others. Specifically, the present specification describes a method of power control that may keep the amount of power applied to sequentially switched antennas constant even as the antenna loads vary.

Specifically, the present specification describes an antenna system. The antenna system includes an array of antennas, each antenna to emit electromagnetic waves. In this example, each antenna is presented with a load that is different from other antennas in the array. The antenna system also includes a control system. The control system includes 1) a single transmitter to sequentially drive antenna sets, 2) a switching device to select, for each activation period in an activation sequence, an antenna set to be driven, and 3) a controller. The controller, for each activation sequence, determines a power output of each antenna and generates an adjusted control signal for the single transmitter such that the power output of at least one antenna is the same as an average value, regardless of a load for the antenna.

The present specification also describes a method. According to the method, it is determined, for each antenna in an array of antennas, a difference between an actual power output for each antenna and an average power output across the array of antennas. A control signal for a single transmitter coupled to each antenna in the array is adjusted such that the power output of the at least one antenna is the same as the average power output across the array, regardless of a load for the antenna. The at least one antenna is driven by the single transmitter based on a first adjusted control signal.

The present specification also describes an electromagnetic treatment device. The electromagnetic treatment device includes a head unit to hold the antennas in predetermined positions relative to the head. The head unit also includes an array of antennas, each antenna to emit electromagnetic waves. In this example, each antenna is presented with a load that is different from other antennas in the array because of how each antenna interfaces to its corresponding portion of the head. The electromagnetic treatment device also includes a control system which includes 1) a single transmitter to drive antenna sets, 2) a switching device to select, for each activation period in an activation sequence, an antenna set to be driven, and 3) a controller. For each activation sequence, the controller 1) determines an actual power output when driving each antenna and 2) generates an adjusted control signal for the single transmitter such that the power output of at least one antenna is the same as an average power output across the array, regardless of a load for the antenna.

As used in the present specification and in the appended claims, the term "activation period" refers to a distinct point in time when a particular antenna, or group of antennas, is active.

Further, as used in the present specification and in the appended claims, the term "activation sequence" refers to a sequence, or pattern of activation periods. Throughout an activation sequence, each antenna may be activated one time. In some examples, for a single activation sequence, only one activation period has an adjusted control signal and other activation periods have no adjusted control signal.

Even further, as used in the present specification and in the appended claims, the term "treatment session" refers to multiple activation sequences, which are sequentially executed. The length of the treatment session may be determined by a caregiver.

Even further, as used in the present specification and in the appended claims, the term "target value" refers to a desired output power value of the antennas based on the treatment parameters.

Even further, as used in the present specification and in the appended claims, the term "average power" refers to the average power output across an array of antennas and may change with each activation sequence. Per activation sequence, the power output of at least one antenna is adjusted to match the average power.

As has been described, the antenna system may activate one or multiple antennas at a given time. In some cases, by changing the phase and/or power of the multiple or single antenna, the system can focus the beams of energy to specific brain areas. By activating multiple antennas, either as sequential groups or simultaneously, a more focused and intense treatment is provided.

To address the issues described above, the present specification describes a power and phase control mechanism for applying output power from a single transmitter, which may be an RF or other type of transmitter, to an array of antennas that may have significantly varying output loading relative to each other. Such a power control mechanism provides consistent radiated output power levels from antennas that may be loaded differently, even with fast sequential switching times from one antenna (or group of antennas) to the next.

The TEMT device for the treatment of Alzheimer's and other diseases and conditions that incorporates the present system is a device that includes an electronic control system and a head unit that has multiple individual antennas for radiating electromagnetic waves, such as radio-frequency waves, into the brain. These antennas can be activated sequentially and/or in combination to produce a radiation pattern that is used as a treatment to the brain. The amount of power that radiates from each antenna may be controlled so that the treatment applied matches what is prescribed and is not too little or too much compared to what is desired.

To achieve a controlled output power level out of an antenna, a system may include a variable output transmitter. The output power of the transmitter may be controlled by way of a power control signal, where a change in this signal results in a corresponding change to the output power of the transmitter. If this control signal is held constant, the output power of the transmitter will also remain constant, as long as the load presented to the transmitter by the antenna remains the same.

However, as the loading of the antenna changes, for example due to physical proximity to absorbing or reflecting material, the load presented to the transmitter also changes, and the output power changes with this load if the control signal is held constant. This is because to drive some loads, the transmitter will output different power levels than when driving into other loads given a constant control signal. Accordingly, a transmitter may use this control signal to vary how hard the transmitter is being driven as the load changes, in order to keep the antenna output constant. To accomplish this mode of operation, a system may employ a power coupler or detector which senses the amount of power coming out of the transmitter and varying the control signal until the target output power is reached. With this scheme in place, as the loading of the antenna changes and the output power changes because of the load, the control signal is adjusted to keep the output power at the target level.

However, in such systems, because a transmitter can respond to control signal changes very quickly, it is very easy to create a situation where the control signal change produces too large of a change in output power. The power detector would sense this and change the control signal, resulting in an oscillation of the power output level. To prevent such a scenario, a circuit may include a damping function to ensure adjustments do not overshoot the target output power, but instead settle towards the target output without oscillation. This damping function can be achieved by adding a low pass filter into the feedback loop that drives the control signal.

Such a control feedback however, may not address the operating conditions of a TEMT device as described herein. The problem arises when a single transmitter and power control loop are used to maintain constant power output levels while rapidly changing antennas that are being driven. That is, in non-TEMT antenna arrays, the antennas in the array are loaded the same way, so the power control signal that is used during one antenna's transmission will produce the correct power output for all of the antennas in the array, which allows for power control over the entire array rather than on an antenna-by-antenna basis.

Figure 1:
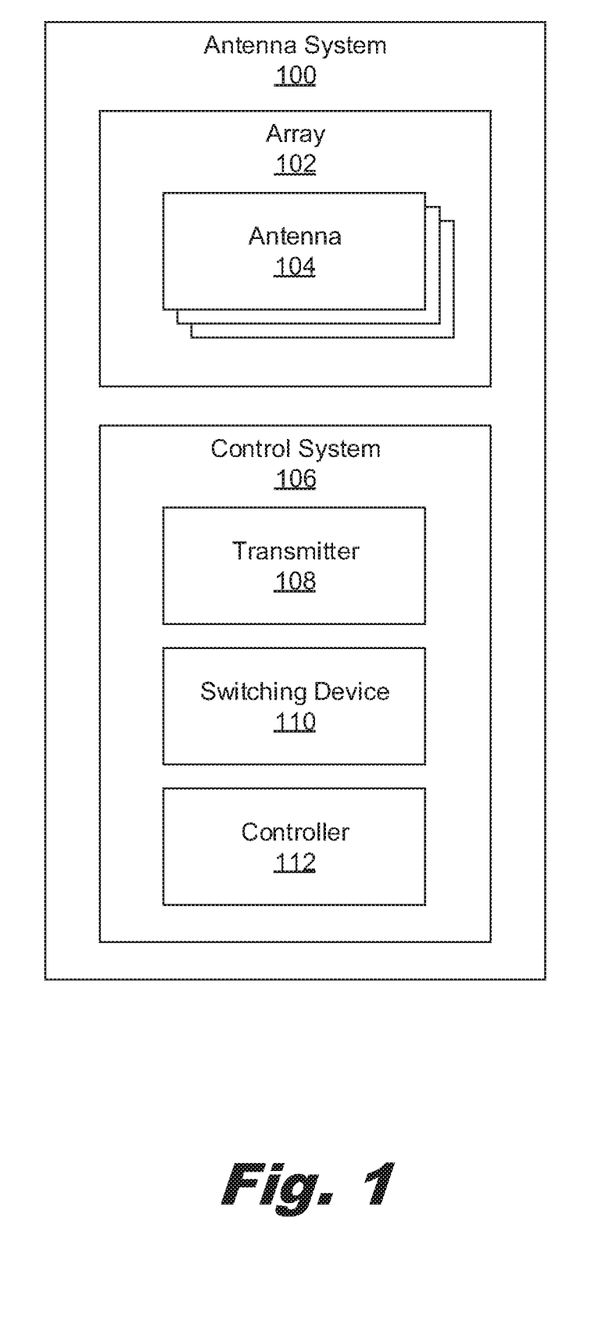
FIG. 1 is a block diagram of an antenna system, according to an example of the principles described herein.

Turning now to the figures, FIG. 1 is a block diagram of an antenna system (100), according to an example of the principles described herein. The antenna system (100) includes an array (102) of antennas (104). Each antenna (104) is to emit electromagnetic waves. As described above, the TEMT device as described herein operates in a unique fashion such that antennas (104) are positioned in various positions on a patient's head, with some being very close to the scalp, while others are further from the scalp because of hair volume. Accordingly, the loading presented to each antenna (104) is very different from other antennas (104) in the array (102), and very different control signals should be presented to the transmitter (108) as each antenna (104) is activated.

The antenna system (100) also includes a control system (106) which includes the single transmitter (108) to sequentially drive antenna (104) sets and a switching device (110) to select, for each activation period in an activation sequence, an antenna set to be driven. The antenna system (100) also includes a controller (112) to 1) determine the actual power output of each antenna (104) given its present load and 2) generate an adjusted control signal for the single transmitter (108) such that the output of at least one antenna is the same as an average power output across the array, regardless of a load for the antenna (104). The controller (112) may sequentially determine an actual power output of each antenna (104) and generate an adjusted control signal for the single transmitter (108) until each antenna (104) in the array (102) has a power output that matches a target value, regardless of a load for the antenna (104).

In one specific example, a TEMT device has an antenna system (100) with 8 antennas (104), and cycles through each antenna (104) at a rate of 217 Hz. This means that each antenna (104) is activated every 4.6 milliseconds (mS), and is on for a duration of 576 microseconds (μS). It may be desirable to have some antennas (104) active for 99% of the time to maximize the efficacy of the treatment session, which translates to needing to switch between antennas (104) in about 5 μS. With the filtering present on general controllers, it would be difficult to run a standard control loop with this timing and still be able to maintain stability and prevent oscillations of output power. However, the adjusted control signal generated by the present control system (106) accounts for antenna (104) load and generates the adjusted control signals during a switch between activation sequences.

To accomplish different power control for each individual antenna (104) with rapid sequential activation, the present control system (106) may split the power control loop into two loops. These control loops may be executed by components disposed in the transmitter (108), the controller (112) or combinations thereof. In a first loop, the power control signal is adjusted based on the average power detected across all driven antennas (104). That is, the controller (112) provides a target power value to the first control loop, and the loop adjusts the power control signal t match the average power to the target power. This first loop is a relatively slow varying loop that adjusts for overall power level changes due to, for example, antennas (104) changing position relative to the patient's head.

The second power control loop runs faster and compares the power detected for each antenna (104) to the average power detected in the first control loop and identifies which antenna (104) produces the power level that is furthest from the average. The second control loop then makes a small adjustment to the power control signal used during that identified antenna's (104) activation period to bring that power level closer to the average. In one example, only one adjustment is made during each activation sequence, and that adjustment is only made to the antenna (104) that produces a power that is furthest from the average detected power of all antennas (104). After many activation sequences and adjustments, all antennas (104) will eventually settle in to produce an output as close as it can to the average power level. At this point, minor adjustments may still be made, which may fall into a pattern of having an antenna (104) adjusted in one direction in one treatment cycle and back in the other direction in the following treatment cycle. In another example, the control system (106) may make adjustments to antennas (104) until their detected power is within a threshold range away from the average power, at which point no further adjustments are made.

To implement this second control loop, a power control signal offset must be maintained for each antenna (104). Accordingly, during the course of running this second control loop, when an antenna (104) is selected, the power control value for the first loop is adjusted by that antenna's (104) power control signal offset from the second control loop, and that value is applied to the transmitter (108) for the time that this antenna (104) is active, i.e., its activation period. This control is subsequently repeated for each antenna (104).

In an alternate embodiment, the second control loop works fast enough to make adjustments to the power control signal at the beginning of the activation period to allow for accurate power control early within the activation period. In yet another embodiment, the second control loop is allowed to act faster at the beginning of the activation period but then is slowed down once the current antenna set's output power is close to the average power. Adjusting the speed of the loop is an adjustment to its low pass filter, or its dampening response.

In one embodiment, the first control loop does not run, and the second control loop becomes a master power control loop and directly controls the power output of each antenna set during its activation period. In this embodiment, the power output for an antenna set is measured by a coupler (328) and compared to the target output by the controller (112). The difference between the actual power and the target power is used to determine an offset, which is used to adjust the power control signal the next time that antenna set comes up in the next activation sequence. This process is repeated for each activation period in the activation sequence, then repeated for each activation sequence in the treatment session.

In one embodiment, the second control loop can be used to implement a factory calibration to account for differences in transmission path loss through the switching device (110) and out to each antenna (104). This can be implemented with the initial offset value for each antenna (104) being loaded with values calculated at the time of production after measuring specific path loss in the paths to each antenna (104). In another example, a calibration value calculated at the time of production can be used as an additional offset to the value measured by a power detector for each antenna (104).

In yet another example, it may be desired that each antenna (104) be driven with a different transmit power level. The different power level may be desirable based upon that antenna's (104) location with respect to desired treatment areas based on anatomical or experimental data showing the need for different treatment levels. In this embodiment, an average value across all antennas (104), i.e., the first control loop, is not calculated, and the second control loop is used to control each antenna's (104) power output compared to that antenna's (104) target output level.

In yet another example, the first control loop is used to determine an average output power value across the array (102), but the second control loop makes adjustments to keep some antennas (104) transmitting at a higher or lower power level than the calculated average value.

As described herein, the output of the second control loop may influence or change the power control voltage of the first control loop. In one particular example, the output of the second control loop can be fed to a different portion of the circuit. In one specific example of such a case, a first control voltage is fed into the transmitter (108) final power amp and the output of the second control loop is used to vary the RF input power level to the final power amp.

The description up to this point has focused on the sequential activation of antennas (104). In this mode, a single antenna (104) is active at one time. That is, the antenna set that is activated includes a single antenna. In this example, the selection of the antenna (104) can be made with a 1-to-N switching device (110). In such a switching device (110), N number of switches each connect the common input to a respective antenna (104) in the antenna array (102). The control signal that comes to the switching device (110) identifies which output should be active, and that switch is set to the closed position to connect the common to the selected output. Examples of switching devices (110) include PIN diodes, transistors, MEMS, or other devices that selectively pass or block RF signals.

In other examples, the antenna set includes multiple antennas (104). For driving multiple antennas (104) at the same time for directing RF treatment to a certain location, the switching device (110) may allow more than one switch to be active at a time, and the power from the transmitter (108) is divided between the active antennas (104). As will be described below, in such an example, the switching device (110) may perform impedance matching to maintain proper impedance presented to the transmitter (108). In this example, instead of sequential activation of individual antennas (104), there is a sequential activation of groups of antennas (104). In this example at least one of a quantity and index of antennas (104) in the antenna set may change per activation sequence. For example, a sequence may be to first activate antennas 1 and 3, then 2 and 4, then 1 and 2 and 3, then 5, then 6 and 7, then 5 and 7, then 5 and 6, then finally 8.

During each step of the sequentially activated antenna sets, both power control loops described above may be running, with the first control loop maintaining average power and the second loop adjusting for each antenna set.

Similar to the single antenna (104) sequencing, the sequencing of multiple antenna sets may have a different target output level for each antenna set. This may be because a set of antennas (104) may be driven at a different power level than a single antenna to get a desired effect. Also, if power is divided between multiple antennas (104) in a set, the power at each antenna (104) is reduced. Accordingly, the controller (112) may increase the power of the transmitter (108) to make up for this power loss. Accordingly, in one example, each antenna set may be adjusted towards a different target output level.

Because the antenna system (100) allows for independent power control between each of the antennas (104) in an array (102), the power control performed by the control system (106) can detect if there is an issue with a single antenna (104) in the array (102) and can take appropriate action. In one embodiment, the control system (106) may detect, for example, one of the antennas (104) not being properly connected and may, as an example, not use that antenna (104) when it comes up in the sequence, but continue to use the other antennas (104) in the array (102). This may be beneficial because a high-power transmitter can incur damage if driving into a damaged or disconnected antenna (104).

In some examples, the error can be detected by simply placing acceptable operation bounds around power control parameters, with an error reported when those bounds are exceeded. This error condition may be indicated to the user through a user interface, may be logged as an error, or handled some other way. Alternatively, the control system (106) could, upon detection of the single antenna (104) error, suspend the entire treatment and indicate the problem in any of the approaches mentioned.

In another example, it may be desired to ensure that each antenna (104) in the set is radiating at the same power level rather than driving the power in parallel to the antennas (104) and hoping that radiation power is the same between the antennas (104). In this example, the control system (106) may include a dedicated power detector after the switch for each antenna path and a variable attenuation device. In this example, the control system (106) monitors the power level at each antenna (104), and attenuates the higher power output antennas (104) until they are all transmitting at the same power. This control loop may operate in conjunction with the control loop previously described that provides the power control signal to the transmitter (108).

With the transmitter (108) driving several antennas (104) in a set and all of the antennas (104) within the set are radiating the same power level, treatment energy is being focused to the desired area within the brain. In some examples, to move the location of focus within the brain, the controller (112) varies a phase of the treatment being fed to one or more of the antennas to steer the beam. The phase of the signal being fed to each antenna (104) can be changed with a dedicated phase shifting network for each antenna.

In this last example, increased functionality of the switching device (110) may be provided via a combination of a switch/attenuator/phase shifter. One embodiment may even combine the power level detection for a particular antenna path into the respective switch, so that for each antenna path, there is a combination of a switch/attenuator/phase shifter/power detector.

While FIG. 1 depicts a particular configuration, it will be evident to those skilled in the art that variations in implementation of these schemes, including locations of circuits within the unit and other implementation details, will still be included in the overall principles as described herein.

Figure 2:
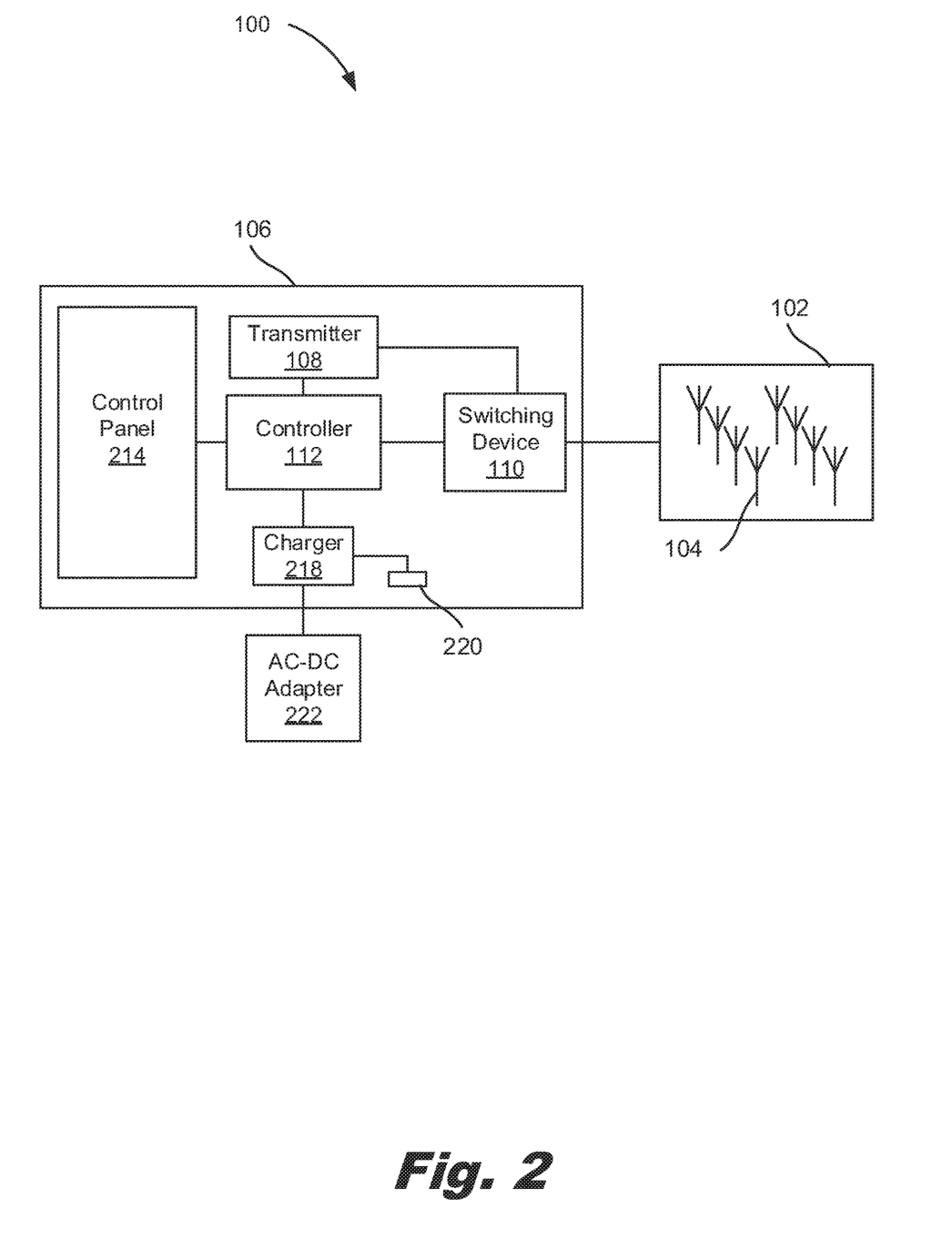
FIG. 2 is a block diagram of an antenna system, according to another example of the principles described herein.

FIG. 2 is a block diagram of an antenna system (100), according to another example of the principles described herein. As described above, the antenna system (100) may be implemented in a transcranial electromagnetic treatment (TEMT) device and includes a control system (106) that drives an array (102) of eight antennas (104) in a head cap worn by a patient receiving treatment. This figure shows three components of the antenna system (100), which are the control system (106), the antenna array (102), and the AC-DC adapter (222) that is plugged into the wall and charges the control system (106). During a treatment, the head unit in which the array (102) is disposed is worn by the patient and the control system (106) may be attached to the patient's arm, for example with a hook and fastener strip. Between treatments, the control system (106) is connected to the AC-DC adapter (222) for charging.

The control system (106) includes the controller (112) which manages the treatments, schedules, and user interface. During a treatment, the controller (112) enables the transmitter (108) to generate and amplify the desired RF waveforms as per the treatment parameters. A power amplifier (PA) of the transmitter then amplifies the RF signal to the levels desired for treatment. The PA output is fed into the switching device (110), which directs the RF signal to the appropriate antenna (104) within the antenna array (102) located in the head unit. As described above, the switching device (110) can have a purely switching function, but could also control power, and could also control phase to the different antennas in the antenna array (102). That is, the controller (112) may vary at least one of a phase of the RF treatment to each antenna within an antenna set, and may vary at least one of a power of the RF treatment for each antenna within an antenna set to control a relative power between each antenna set. The control system (106) may also include a control panel (214) that provides the interface to the user, is used to start or stop treatments, and provides feedback and information to the user, such as treatment status and battery level.

The control system (106) may be powered by an internal battery (220) that provides enough power to run the control system (106) and complete the treatments. The charging device (218) charges the battery (220) when the AC-DC adapter (222) is present. In one example, the controller (112) gets charge status and AC-DC adapter (222) presence from the charging device (218) and displays status on the control panel (214).

Figure 3:
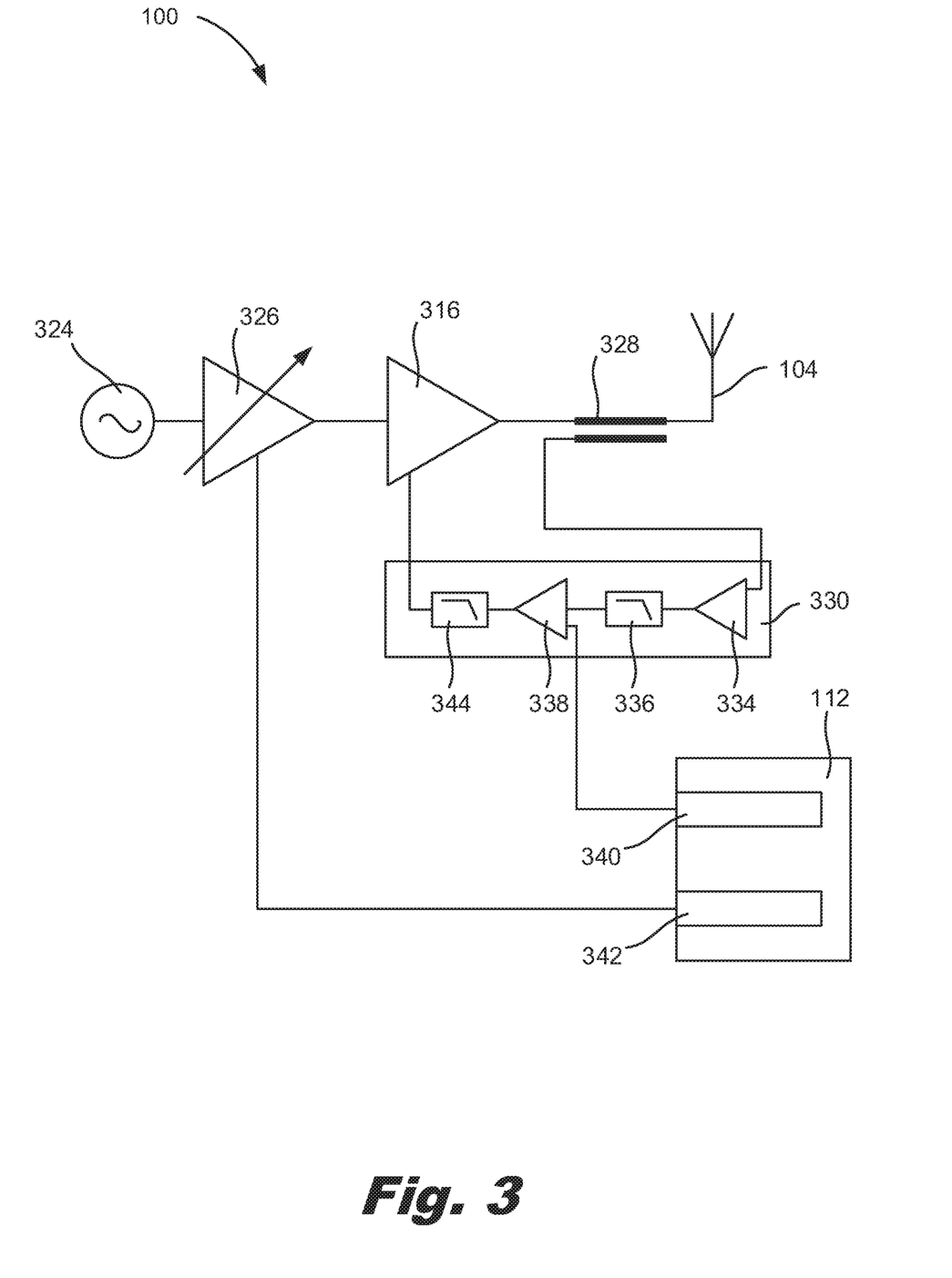
FIG. 3 depicts the antenna system, according to an example of the principles described herein.

FIG. 3 depicts an antenna system (100), according to an example of the principles described herein. In this example, the transmitter (FIG. 1, 108) includes an oscillator (324) to generate the RF signal. In one example, the oscillator (324) is a phase-locked loop, or PLL, which is modulated with the desired modulation. The RF signal is then fed into a variable gain amplifier (VGA) (326) of the transmitter (FIG. 1, 108), which can be controlled in an analog or digital mode. In an example, the variable gain amplifier (326) is controlled digitally by setting a value in a power control register within the transmit integrated circuit (IC). The output of the variable gain amplifier (326) is then fed into a power amplifier (316) of the transmitter. This power amplifier (316) may be a high output power device capable of driving at the higher output levels desired for treatment. The output level of the power amplifier (316) should be accurately controlled by an active power control system (330), which ensures that the transmitter (FIG. 1, 108) is always outputting a constant level, regardless of the load presented to the transmitter (FIG. 1, 108). This is advantageous, because if the load to the power amplifier (316) changes and power is not adjusted accordingly, the power amplifier (316) may output a power level above its rating and may quickly become damaged. The output of the power amplifier (316) is fed through the coupler (328) to the antenna (104), where it is radiated into the air.

The power control system (330) controls the output power of the power amplifier (316) by measuring the output power through the coupler (328) and rectifying the coupled power to produce a voltage proportional to the output power (circuitry not shown). This voltage is then amplified with amplifier (334), filtered through a first low pass filter (336), and compared to a control voltage by the differential amplifier (338). The control voltage for comparison comes from the control voltage generator (340) in the controller (112), which control voltage generator (340) may be a power control digital-to-analog converter (DAC). The difference between the scaled output power and control voltage is filtered through a second low pass filter (344) and fed to the control input of the secondary amplifier (328). While FIG. 3 depicts a particular architecture for the power control system (330), the details in this power control device may be integrated, combined, or separated from one another in actual implementation. For example, the first low pass filter (336) may be integrated with the amplifier (334) to create an amplifier with a low pass filtered response. Moreover, the power control system (330) may be disposed in either the transmitter (FIG. 1, 108) or the controller (112).

The controller (112) also includes a VGA control signal generator. The controller (112) in FIG. 3 sets the transmitter (FIG. 1, 108) to transmit at a certain power output level. For a particular output level, the controller (112) will set the variable gain amplifier (326) to a known output level. Accordingly, in this example, the VGA control signal generator is a fixed value control signal generator (342), which provides power control to the variable gain amplifier (326). In this example, the controller (112) performs open loop power control, in that there is no feedback to close the loop and ensure that the output is maintained at the desired target output level. An alternate embodiment may have a closed power control loop that drives the variable gain amplifier (326) to the output set by the fixed value control signal generator (342). The output of the variable gain amplifier (326) is set to a particular output level based on the desired output level at the antenna (104) and the gain and efficiency performance of the power amplifier (316). The controller (112) also sets the control voltage for the differential amplifier (338) with the control voltage generator (340), i.e., the power control DAC. Through calibration, the controller (112) knows what control voltages correspond to what output power at the antenna (104).

During operation, the controller (112) sets up for the target output level at the antenna (104) and the power control device (330) maintains that power level at the antenna (104). As the antenna (104) load changes, the load presented to the power amplifier (316) changes, which changes the power level that the power amplifier (316) outputs, based on the load presented and the characteristics of the transmitter (FIG. 1, 108). As that power changes, the level out of the power coupler (328) changes, which feeds through and changes the detected voltage going into the differential amplifier (338), which then changes the power control to the transmitter (FIG. 1, 108), moving its output power back to the target level with this new antenna (104) load.

Figure 4:
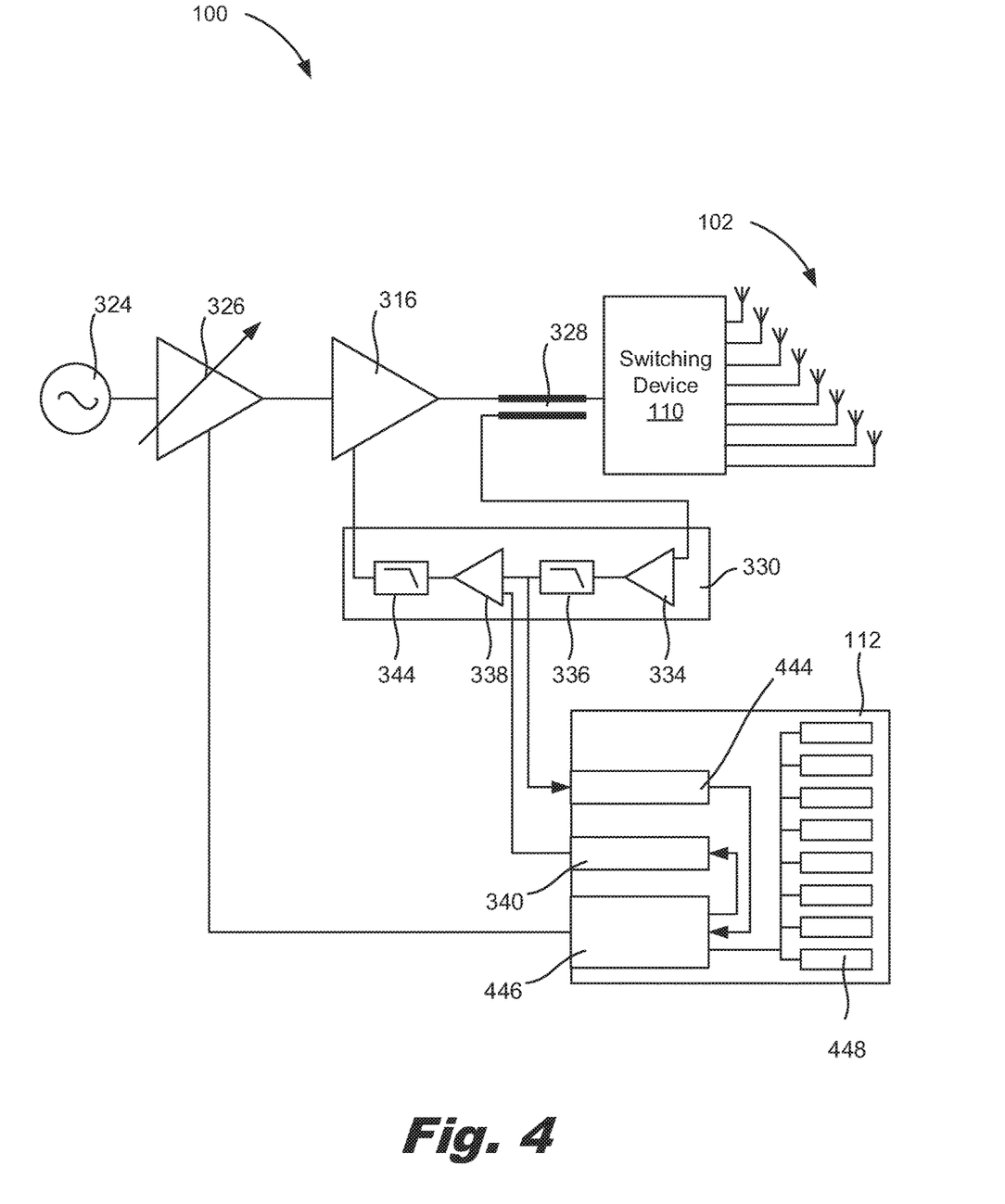
FIG. 4 depicts the antenna system, according to another example of the principles described herein.

FIG. 4 depicts an antenna system (100), according to an example of the principles described herein. This figure shows elements that are in addition to what is found in FIG. 3. Similar to FIG. 3, the RF signal is generated by the oscillator (324) and fed into variable gain amplifier (326), which is then fed into the power amplifier (316). The final transmitter (FIG. 1, 108) output power is coupled through coupler (328) and fed into the power control system (330), which operates similarly as described in FIG. 3. That is, the coupled output is rectified and amplified by the amplifier (334), sent through a first low pass filter (336), and fed into the differential amplifier (338), where it is compared to a control voltage, filtered by a second low pass filter (334), and fed into the control input of the power amplifier (316).

FIG. 4 shows the output of the coupler (328) being fed into a switching device (110). The switching device (110), under control of the controller (112), directs the RF to one of the antennas (FIG. 1, 104) in the antenna array (102). In another example, the switching device (110) also can direct power to multiple antennas (FIG. 1, 104) at once, can adjust the power to each of the multiple antennas (FIG. 1, 104), and can adjust the phase of the signal fed to each of the multiple antennas (FIG. 1, 104).

As the controller (112) switches antennas (FIG. 1, 104) in and out, the power control system (330) maintains that the average power across all of the antennas (FIG. 1, 104) will remain constant. However, this may be done with some of the antennas (FIG. 1, 104) having higher output power while others have lower output power, provided that the average of all antennas (FIG. 1, 104) will be regulated to the level corresponding to the control that is output by the control voltage generator (340). This is because the low pass filtering in the first low pass filter (336) and the second low pass filter (344) will produce a slower response than the time it takes to complete an antenna sequence, so the power control system (330) does the averaging of the power level of the entire antenna sequence.

In this example, the controller (112) includes additional components and makes adjustments so that all antennas (FIG. 1, 104) are outputting the same power level rather than some high and some low. The controller (112) accomplishes this by reading the detected power with a voltage detector such as a power detect analog-to-digital converter (ADC) (444) for each antenna (FIG. 1, 104). If the detected output of a particular antenna (FIG. 1, 104) is too high or too low, the variable gain amplifier (326) will be adjusted for that antenna (FIG. 1, 104) to bring it closer to the other antennas (FIG. 1, 104). Each time an antenna (FIG. 1, 104) is active, the detected power is read by the ADC (444), and an offset value for that antenna (FIG. 1, 104) is calculated and stored in an offset memory storage device (448) for that antenna (FIG. 1, 104). For simplicity in FIG. 4 just one offset memory storage device (448) is indicated with a reference number. The next time that antenna (FIG. 1, 104) is active, the VGA control signal generator (446) offsets the control signal for the variable gain amplifier (326) by the offset stored in the offset memory storage device (448) for that antenna (FIG. 1, 104). Through each cycle of antennas (FIG. 1, 104), one or more offset values in the offset memory storage device (448) are calculated and adjusted. Through this process, after several iterations, the offset values will settle to their final values, and the power outputs across antennas (FIG. 1, 104) will be equal.

Once this second power control loop has settled, if the load on a single antenna (FIG. 1, 104) changes, the power detect ADC (444) will measure the corresponding power change, and the controller (112) will adjust the offset value for that antenna (FIG. 1, 104) until that antenna's (FIG. 1, 104) output power is brought back to be the same level as the other antennas (FIG. 1, 104).

If for some reason there is a difference in loss between two different antenna paths, either through the switching device (110) or because of routing on the printed circuit board (PCB), the controller (112) can store this loss as an additional offset value, and offset all of the readings of the power detect ADC (444) for that particular antenna (FIG. 1, 104) by that offset. Doing this can ensure that power output is the same to each antenna (FIG. 1, 104), even if the path loss to each antenna (FIG. 1, 104) is different.

Figure 5:
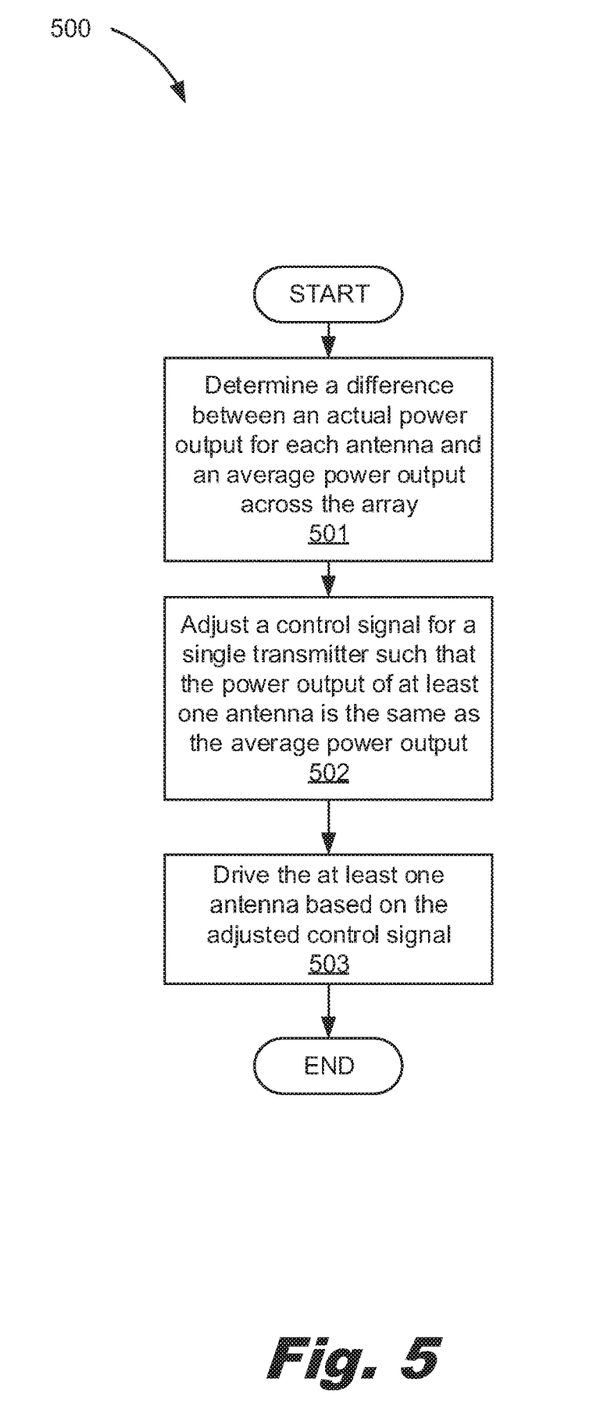
FIG. 5 is a flowchart of a method of controlling the antenna system, according to an example of the principles described herein.

FIG. 5 is a flowchart of a method (500) of controlling the antenna system (FIG. 1, 100), according to an example of the principles described herein. According to the method (500), it is determined (block 501), for each antenna (FIG. 1, 104) in an array (FIG. 1, 102) of antennas (FIG. 1, 104), a difference between an actual power output for each antenna (FIG. 1, 104) and an average power output across the array. Note that in some examples, the average value to which the actual antenna power output at a single antenna is compared is not the target value. That is, the target value is what the controller (FIG. 1, 112) is trying to regulate the output power to, based on the treatment parameters. The controller (FIG. 1, 112) then sets up control loops to drive the antennas (FIG. 1, 104) towards the target power. If the set includes a single antenna system, that would be it. However, in the case of a multi-antenna system, it is first determined which antenna to adjust, so each antenna's output is compared to an average power output of all the antennas, and not the target power. In other words, the target power is a desired output based on the treatment parameters, but any adjustments are made on the antenna that is furthest from the average power (which may not be equal to the target power as the loops are settling).

After a few activation sequences, the average power output should match the target power. However, as adjustments are being made, the average power may not equal the target power. Accordingly, following driving of the at least one antenna (FIG. 1, 104) based on the first adjusted control signal, the method may include determining a new average power output across the array (FIG. 1, 102) of antennas (FIG. 1, 104). The controller (FIG. 1, 112) again determines, for each antenna (FIG. 1, 104) in the array (FIG. 1, 102), a difference between an actual power output for each antenna (FIG. 1, 104) and this new average power output and adjusts the control signal for a single transmitter (FIG. 1, 108) such that a power output of at least one antenna (FIG. 1, 104) is the same as the new average power output. The antenna (FIG. 1, 104) adjusted in the second activation sequence may not be the same as the antenna adjusted in the first activation sequence. The second antenna (FIG. 1, 102) is then driven via the single transmitter based on the second adjusted control signal. This process is repeated until the power output in each antenna (FIG. 1, 104) in the array (FIG. 1, 102) is the same as the target value.

Adjusting the at least one antenna (FIG. 1, 104) towards the average power and not the target power reduces the number and length of activation sequences to stabilize the antenna array (FIG. 1, 102) power output. This may be done by the antenna system (FIG. 1, 100) described in FIGS. 1-4.

Then, during an activation period and based on the determined difference, a control signal for the transmitter (FIG. 1, 108) is adjusted (block 502) such that the output of at least one antenna (FIG. 1, 104) is the same as the average value, regardless of a load for the antenna (FIG. 1, 104). This process may be repeated until all antennas have an output that matches the average power output, which when stabilized may match the target value.

As described above, in some examples, the at least one antenna (FIG. 1, 104) for which the control signal is adjusted may be the antenna (FIG. 1, 104) within the array (FIG. 1, 102) with the greatest difference. In this example, the activation period in which the control signal is adjusted for this largest offset antenna (FIG. 1, 104) is the only activation period of an activation sequence with an adjusted control signal. During subsequent activation sequences, different activation periods may include adjusted signals. The at least one antenna (FIG. 1, 104) is then driven (block 503) by the single transmitter (FIG. 1, 108) based on the adjusted control signal. That is, the adjusted control signal is passed to the power amplifier (FIG. 3, 316) to adjust the output power of the RF treatment that is fed to the antenna.

Figure 6:
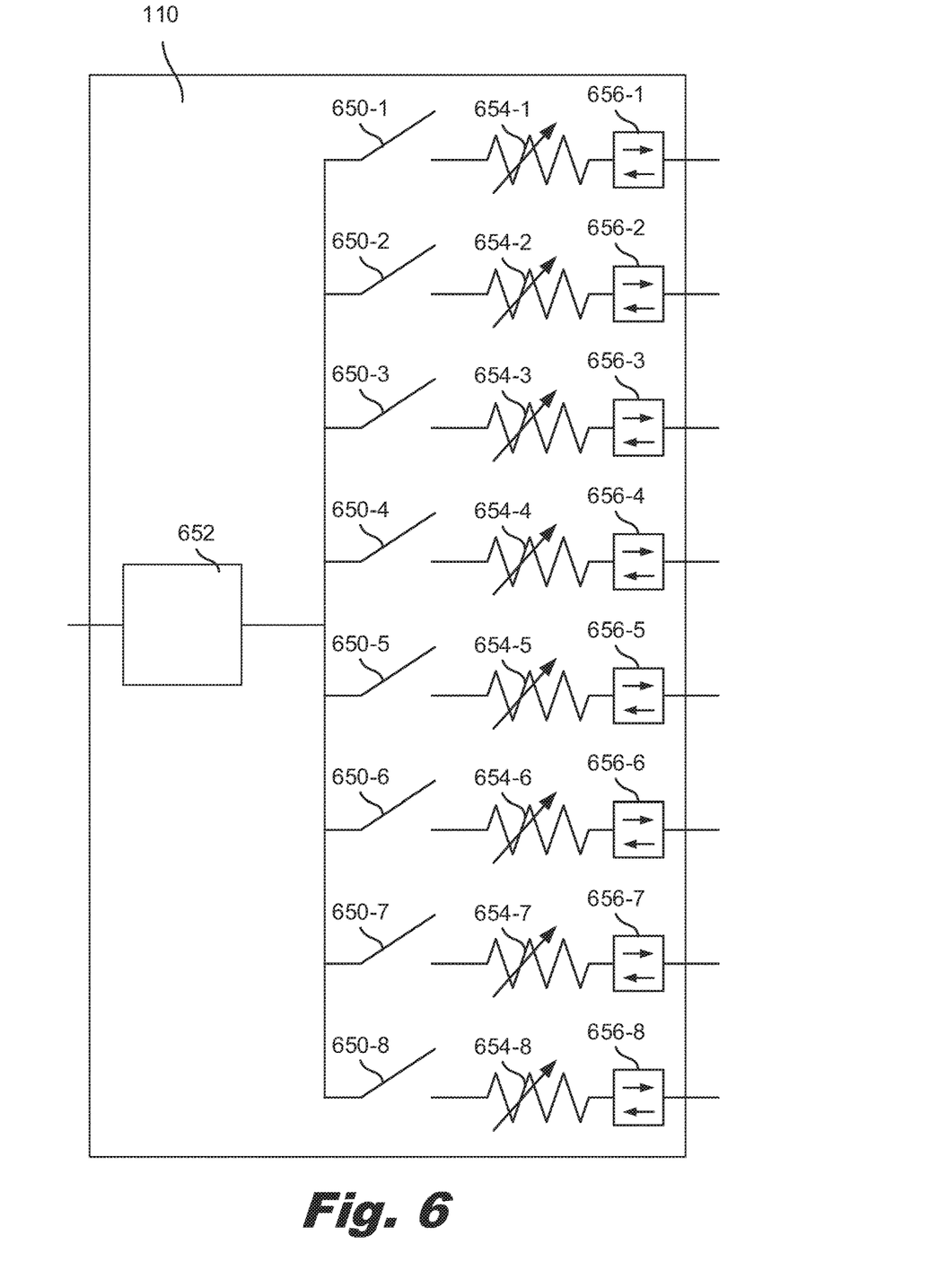
FIG. 6 depicts an example of a switching device that controls antenna selection, power, and phase, according to an example of the principles described herein.

FIG. 6 depicts an example of a switching device (110) that controls antenna (FIG. 1, 104) selection, power, and phase, according to an example of the principles described herein. In this example, the switching device (110) can switch multiple antennas (FIG. 1, 104) on at one time, adjust the power between antennas (FIG. 1, 104) that are switched on at the same time, and adjust the phase between antennas (FIG. 1, 104) that are switched on at the same time. In this figure, one input and eight outputs are shown, although the implementation can be scaled to any number of outputs. Also, in one case, the switching device (110) may include a subset of the elements shown. For example, the switching device (110) may include the phase shift networks but not the components that adjust power levels.

The front end of the switching device (110) includes a single input that is distributed to eight switches (650-1 650-2, 650-3, 650-4, 650-5, 650-6, 650-7, 650-8) in parallel. Each of these switches (650) may be mechanical, electro-mechanical, or electrical. Because the switches (650) are connected in parallel, RF power will be distributed across the switch (650) outputs relatively equally. For example, if two switches (650) are active, the output power level at each of the switch (650) outputs will be approximately half of the input power to the switching device (110), due to the power being divided and the loss incurred from the switch (650) itself. Accordingly, if power is being distributed between multiple antennas (FIG. 1, 104), the input power to the switching device (110) may need to be adjusted to offset that less power is going to each antenna (FIG. 1, 104). Because of the impedance change of multiple switches (650) being active, an impedance matcher (652), either static or dynamic, may be employed to keep the loading to the device driving this bank constant.

After the switches (650) on each path is a variable attenuator (654-1, 654-2, 654-3, 654-4, 654-5, 654-6, 654-7, 654-8) to adjust the output power on each branch. In some examples, power adjustments are only down and not up, since an adjustment up would require an active gain circuit. Power down adjustments with the variable attenuators (654) is limited, as a significant power reduction would produce a large amount of heat which may not be tolerated by the switching device (110) circuitry. But using the architecture depicted in FIG. 6, the overall power to the switching device (110) could be increased and selective antenna paths could be set to reduce power on those paths, allowing for control of relative output power between antennas (FIG. 1, 104).

After the attenuators (654) on each path is a phase shifter (656-1, 656-2, 656-3, 656-4, 656-5, 656-6, 656-7, 656-8) that can shift the phase on a particular path as per a control signal. Shifting relative phase between antennas (FIG. 1, 104) allows for beam forming or steering of the radiated signal.

Figure 7:
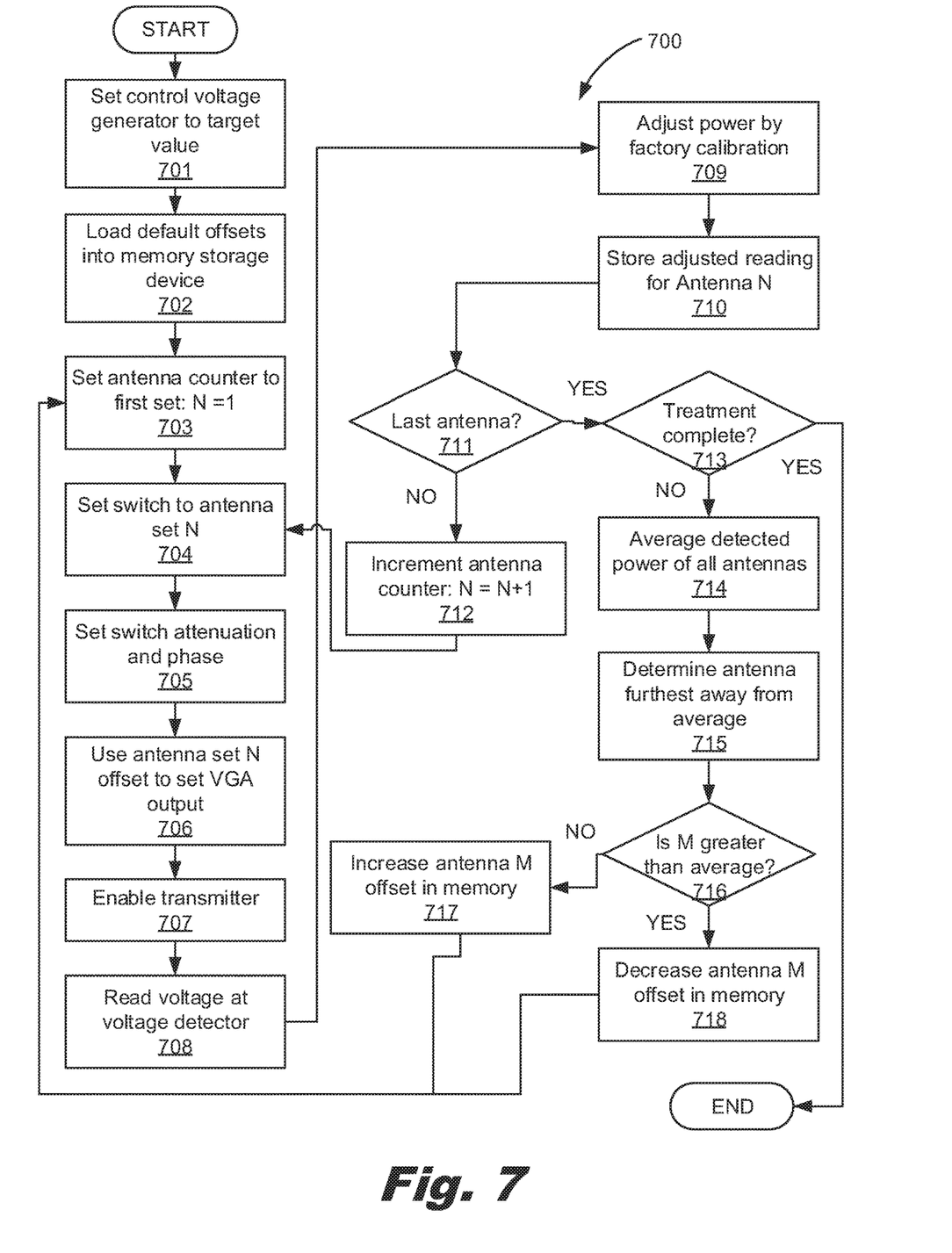
FIG. 7 is a flowchart of a method of controlling the antenna system, according to another example of the principles described herein.

FIG. 7 is a flowchart of a method (700) of controlling the antenna system (FIG. 1, 100), according to another example of the principles described herein. The method (700) starts when the user or medical professional indicates that a treatment should begin. This indication should happen after the head unit has been put on the patient and the TEMT device is prepared. At the start of the treatment before the therapy begins, the control voltage is set (block 701) to a target value. Default offsets for the individual antenna are loaded (block 702) into the offset memory storage device(s) (FIG. 4, 448), and the antenna counter is set (block 703) to the first antenna set.

In this example, each antenna (FIG. 1, 104) set will be sequentially cycled until the treatment is complete. If multiple antennas (FIG. 1, 104) are being activated simultaneously for focused treatment within the brain, the flowchart is the same, but "N" refers to a group of active antennas (FIG. 1, 104) rather than a single antenna (FIG. 1, 104). In one example, the entire sequence is completed and at the end of each sequence, just a single antenna offset is updated. In other examples, more than one antenna offset may be updated with each sequence completion. In some examples, an entire treatment session may be one hour, and an activation sequence is completed in 4.6 mS (corresponding to an antenna pulse repetition rate of 217 Hz). This results in 781,200 sequences (and opportunity for offset adjustment) occurring in a treatment session.

As an activation sequence is cycled through, the flow starts with the first antenna (FIG. 1, 104) or antenna (FIG. 1, 104) group in the array (FIG. 1, 102). The switching device (FIG. 1, 110) is first set (block 704) for that antenna (FIG. 1, 104) or antenna (FIG. 1, 104) group N. In the case of an antenna (FIG. 1, 04) group, attenuation and phase is also set (block 705) in the switching device (FIG. 1, 110). The offset for antenna set N is then read from the offset memory storage device (FIG. 4, 448) and used (block 706) to set the output power of the variable gain amplifier (FIG. 3, 326). At this point, the gain path has been set up, so the controller (FIG. 1, 112) enables (block 707) the transmitter (FIG. 1, 108) to generate the RF pulse for the proper duration.

Before the RF pulse is completed, the controller (FIG. 1, 112) reads (block 708) the detected power from the coupler (FIG. 3, 328) and amplifies what is fed into the power detect ADC (FIG. 4, 444). If there is any factory calibration for antenna (FIG. 1, 104) set N because of any different path loss compared to other antennas (FIG. 1, 104), the calibration offset is adjusted (block 709). The reading is then stored (block 710) locally by the controller (FIG. 1, 112) so that an average of all antennas (FIG. 1, 104) in the sequence can be calculated and so the reading can be used in the power control algorithm.

At this point, a check (block 711) is done to see if this is the last antenna (FIG. 1, 104) in the activation sequence. If it is not the last antenna (FIG. 1, 104) in the activation sequence (block 711, determination NO), the antenna counter is incremented (block 712) and the next antenna sequence is processed. If it was the last antenna in the activation sequence (block 711, determination YES), a check (block 713) is done to see if the treatment session is complete. If the treatment session is not complete (block 713, determination NO), the controller (FIG. 1, 112) uses the stored power readings of all antennas to calculate (block 714) the average detected power across the antennas (FIG. 1, 104). The controller (FIG. 1, 112) then compares each individual antenna reading to the average, and determines (block 715) which antenna (FIG. 1, 104) had a power reading furthest from the average. It is this antenna that will be adjusted in this activation sequence, which is referred to as antenna or antenna group M. If the power reading for antenna set M is greater than the average (block 716, determination YES), the power of the variable gain amplifier (FIG. 3, 326) should be lowered the next time antenna set M is active, so the offset is decreased (block 718) by a small value and stored in the offset memory storage location (FIG. 4, 448) for antenna set M (block 718). The offset adjustment may be small. That is, this change in power level will change the average power of all antennas (FIG. 1, 104) and create an adjustment of the first power control loop in the system. Accordingly, for system stability, small changes should be made. If the power reading for antenna set M is less than the average (block 716, determination NO), the offset value for antenna set M is increased (block 717) by a small amount and stored. As described above, in some examples, the method (700) includes one adjustment made per activation sequence, although an alternate example may only make an adjustment if the largest deviation from average exceeded some threshold. At this point the antenna counter is reset to the first antenna (block 703) and the activation sequence is repeated. If at the end of an activation sequence, it is determined that the treatment is complete (block 713, determination YES), the amplifiers are powered down and the treatment is concluded.

Figure 8:
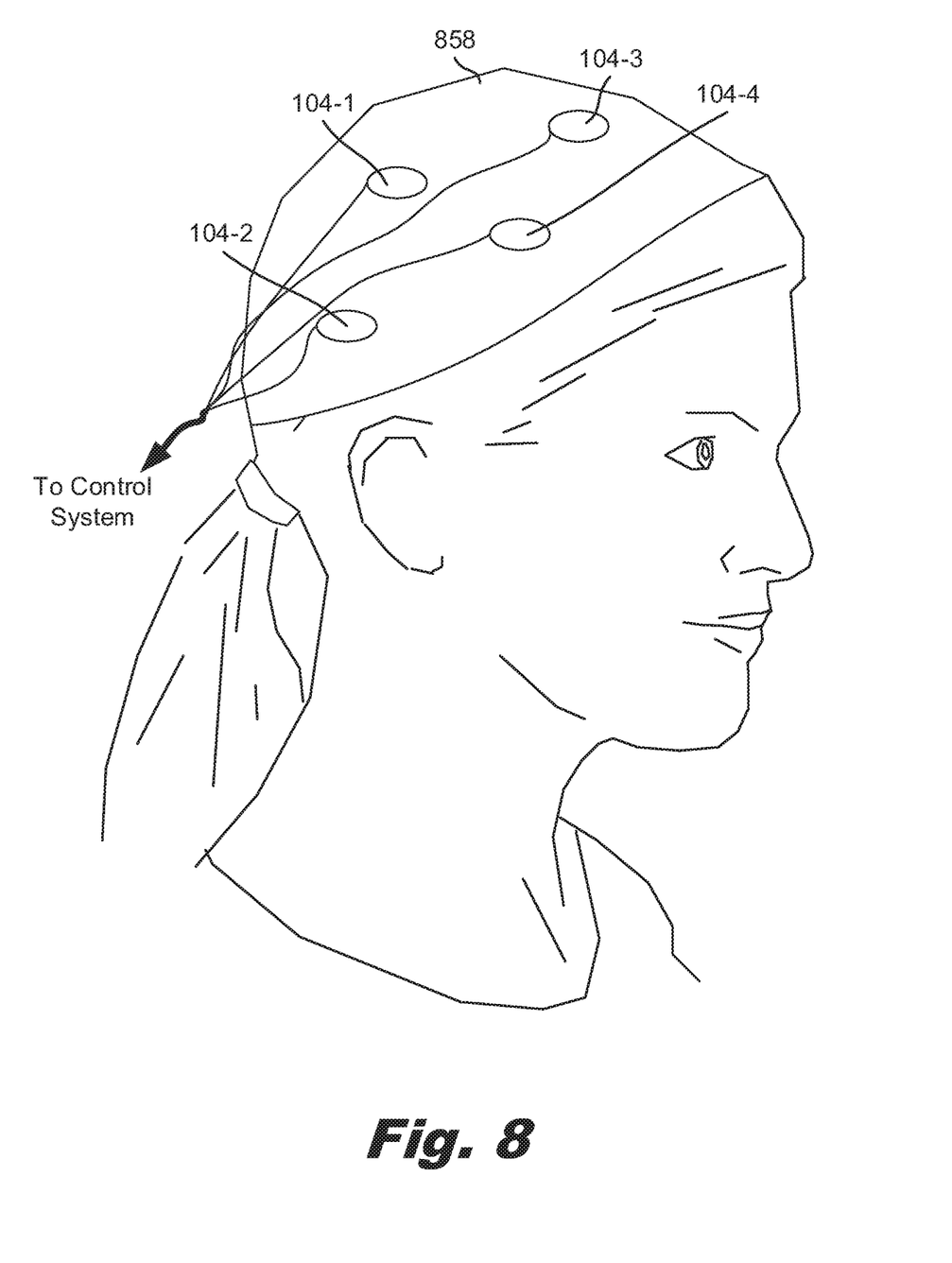
FIG. 8 depicts an electromagnetic treatment device with the antenna system, according to an example of the principles described herein.

FIG. 8 depicts an electromagnetic treatment device with the antenna system (FIG. 1, 100), according to an example of the principles described herein. The electromagnetic treatment device includes a head unit (858) to hold antennas in predetermined positions relative to the head of the human subject. The head unit (858) also includes an array (FIG. 1, 102) of antennas (104). As described above, each antenna (104) is to emit electromagnetic waves and is presented with a load that is different from other antennas (104) in the array (FIG. 1, 102). Note that FIG. 8 depicts antennas (104) on one side of the head region. The opposite side of the head region may include similarly positioned antennas (104).

The electromagnetic treatment device also includes the control system (FIG. 1, 106) as depicted in FIG. 1. That is, the control system (FIG. 1, 106) includes a single transmitter (FIG. 1, 108) to drive the antenna sets (104) and a switching device (FIG. 1, 110) to select, for each activation period in an activation sequence, an antenna (FIG. 1, 104) set to be driven. The control system (FIG. 1, 106) also includes a controller (FIG. 1, 112) which determines an actual power output on each antenna (FIG. 1, 104) and generates an adjusted control signal for the single transmitter (FIG. 1, 108) such that the output of at least one antenna (FIG. 1, 104) is the same as a first adjusted power value, regardless of a load for the antenna (FIG. 1, 104).

The preceding description has been presented only to illustrate and describe the subject matter presented herein. It is not intended to be exhaustive or to limit the subject matter to any precise form disclosed. Many modifications and variations are possible in light of the above teaching.

The examples descried herein were chosen and described in order to best explain the principles of the subject matter and its practical application. The preceding description is intended to enable others skilled in the art to best utilize the subject matter in various embodiments and with various modifications as are suited to the particular use contemplated.

What is claimed is:

1. An antenna system, comprising:
   an array of antennas, each antenna to emit electromagnetic waves, wherein each antenna is presented with a load that is different from other antennas in the array; and
   a control system, comprising:
      a single transmitter to sequentially drive antenna sets;
      a switching device to select, for each activation period in an activation sequence, an antenna set to be driven; and
      a controller to:
         determine an actual power output of each antenna;
         determine a difference between the actual power output for each antenna and an average power output of all antenna sets; and
         generate an adjusted control signal for the single transmitter based on the difference between the actual power output for each antenna and an average power output of all antenna sets such that the power output of each antenna is controlled to match a target power for that antenna, regardless of a load for the antenna.

2. The system of claim 1, wherein the antenna set includes at least one of:
   a single antenna to be active at a given time; and
   multiple antennas to be active at the given time, wherein a driving signal from the single transmitter is divided between the multiple antennas.

3. The system of claim 1, wherein multiple antennas in the array focus beams in a particular direction within a subject.

4. The system of claim 1, wherein the controller sequentially determines the actual power output of each antenna and generates, per activation sequence, the adjusted control signal for the single transmitter until at least one antenna in the array has a power output that matches the average power output across all antenna sets, regardless of a load for the antenna.

5. The system of claim 1, wherein the controller generates the adjusted control signal during a switch between activation periods.

6. The system of claim 1, wherein the controller varies a phase of at least one antenna output within an active set to steer a beam.

7. The system of claim 1, wherein the controller varies a power of at least one antenna output within an active set to control a relative power between each antenna set.

8. The system of claim 1, wherein the controller dampens the adjusted control signal to ensure sequential adjustments do not overshoot.

9. The system of claim 1, wherein the switching device comprises at least one of:
   a variable attenuator per antenna coupled to a respective switch;
   a phase shifter per antenna coupled to a respective variable attenuator; and
   an impedance matcher.

10. The system of claim 1, wherein the control system further comprises at least one of:
    a charging device;
    an internal battery; and
    a control panel.

11. The system of claim 1:
    further comprising a power control system disposed in at least one of the transmitter and the controller; and
    wherein:
       the transmitter comprises:
          an oscillator to generate a radio frequency (RF) signal;
          a variable gain amplifier (VGA) coupled to the oscillator to receive the RF signal;
          a power amplifier coupled to the VGA to receive the RF signal from the VGA; and
          a coupler coupled to the power amplifier to receive the RF signal from the power amplifier, the coupler further coupled to the power control system; and
       the controller comprises:
          a control voltage generator to generate a control voltage to compare to the RF signal provided by the coupler; and
          a (VGA) control signal generator.

12. The system of claim 11, wherein the VGA control signal generator comprises a fixed value control signal generator.

13. The system of claim 11, wherein:
    the controller comprises:
       a voltage detector to measure the power output of each antenna;
       an offset memory storage device to store an offset value for each antenna comprising a difference between the measured power output and a target power output; and
    the VGA control signal generator is to generate the VGA control signal based on a detected voltage and an offset.

14. A method, comprising:
    determining, for each antenna in an array of antennas, a difference between an actual power output for each antenna and an average power output of all antenna sets;
    adjusting, based on the determining a difference between an actual power output for each antenna and an average power output of all antenna sets, a control signal for a single transmitter coupled to each antenna in the array such that a power output of each antenna is controlled to match a target power for that antenna; regardless of a load for the antenna; and driving, via the single transmitter, the at least one antenna based on a first adjusted control signal.

15. The method of claim 14, wherein:

the at least one antenna is an antenna within the array of antennas with a greatest difference; and an activation period in which the control signal is adjusted is the only activation period within an activation sequence with an adjusted control signal.

16. The method of claim 14, further comprising, detecting a defective antenna based on the difference.

17. The method of claim 14, further comprising adjusting a phase of an output for each antenna in the antenna set to focus the electromagnetic waves to a particular location on a subject.

18. An electromagnetic treatment device comprising:

a head unit to hold antennas in predetermined positions relative to the head, the head unit comprising an array of antennas, each antenna to emit electromagnetic waves, wherein each antenna is presented with a load that is different from other antennas in the array; and a control system, comprising:

a single transmitter to drive antenna sets;

a switching device to select, for each activation period in an activation sequence, an antenna set to be driven; and a controller to:

determine a power output of each antenna;

determine a difference between the actual power output for each antenna and an average power output of all antenna sets; and generate an adjusted control signal for the single transmitter based on the difference between the actual power output for each antenna and, an average power output of all antenna sets such that the power output of at least one antenna is controlled to match a target power for that antenna, regardless of a load for the antenna.

19. The electromagnetic treatment device of claim 18, further comprising an AC-DC adapter to charge the control system.

20. The electromagnetic treatment device of claim 18, wherein the electromagnetic treatment device is for treatment or prevention of neurodegenerative diseases and conditions and for the enhancement of unimpaired cognitive function.

* * * * *